(12) United States Patent
Cane et al.

(10) Patent No.: US 11,443,836 B2
(45) Date of Patent: Sep. 13, 2022

(54) SYSTEM AND METHOD FOR THE RECORDING OF PATIENT NOTES

(71) Applicant: Modernizing Medicine, Inc., Boca Raton, FL (US)

(72) Inventors: Daniel Cane, Boynton Beach, FL (US); Michael Sherling, Boca Raton, FL (US)

(73) Assignee: MODERNIZING MEDICINE, INC., Boca Raton, FL (US)

( * ) Notice: Subject to any disclaimer, the term of this patent is extended or adjusted under 35 U.S.C. 154(b) by 178 days.

(21) Appl. No.: 16/775,637

(22) Filed: Jan. 29, 2020

(65) Prior Publication Data

US 2020/0168303 A1 May 28, 2020

Related U.S. Application Data

(63) Continuation of application No. 16/268,929, filed on Feb. 6, 2019, now abandoned, which is a continuation
(Continued)

(51) Int. Cl.
*G16H 10/20* (2018.01)
*G06F 16/33* (2019.01)
(Continued)

(52) U.S. Cl.
CPC ......... *G16H 10/20* (2018.01); *G06F 16/3344* (2019.01); *G06F 16/9535* (2019.01);
(Continued)

(58) Field of Classification Search
CPC ........ G16H 10/20; G16H 10/60; G16H 15/00; G16H 40/63; G16H 70/20; G06F 16/3344; G06F 16/9535
(Continued)

(56) References Cited

U.S. PATENT DOCUMENTS 4,839,822 A 6/1989 Dormond et al.
5,065,315 A 11/1991 Garcia
(Continued)

OTHER PUBLICATIONS

NexTech The Complete Solution, PDF available from http://www.nextech.com/products/Software-brochures.aspx NextechPractice 2011—Designed for Dermatology (not admitted to be prior art; last viewed on Aug. 15, 2011).
(Continued)

*Primary Examiner* — Michael Tomaszewski
(74) *Attorney, Agent, or Firm* — K&L Gates LLP (57) ABSTRACT

A system and method for recording patient notes by a physician. In one embodiment, the system includes a server comprising: a database; an input module, a display module; and an adaptive notes generation module in the server in communication with the database, the input module and the display module, the adaptive notes generation module receiving input data from the input module and the database and in response to the input data from the input module and the database, automatically generating a plurality of notes and note options. In one embodiment, the method includes the steps of: providing an input screen; inputting data; accessing a database to obtain patient data in response to data input to the input screen; and generating domain specific notes and note options in response to patient data and input to the input screen.

23 Claims, 10 Drawing Sheets

Related U.S. Application Data of application No. 15/235,631, filed on Aug. 12, 2016, now abandoned, which is a continuation of application No. 13/191,030, filed on Jul. 26, 2011, now abandoned.

(60) Provisional application No. 61/370,250, filed on Aug. 3, 2010.

(51) Int. Cl.
| | |
|---|---|
| *G06F 16/9535* | (2019.01) |
| *G16H 40/63* | (2018.01) |
| *G16H 10/60* | (2018.01) |
| *G16H 15/00* | (2018.01) |
| *G16H 70/20* | (2018.01) |

(52) U.S. Cl.
CPC ............ *G16H 10/60* (2018.01); *G16H 15/00* (2018.01); *G16H 40/63* (2018.01); *G16H 70/20* (2018.01)

(58) Field of Classification Search
USPC .......................................................... 705/2–3
See application file for complete search history.

(56) References Cited

U.S. PATENT DOCUMENTS

| | | | |
|---|---|---|---|
| 5,265,010 A | 11/1993 | Evans-Paganelli et al. | |
| 5,660,176 A | 8/1997 | Illiff | |
| 5,924,074 A | 7/1999 | Evans | |
| 6,047,259 A | 4/2000 | Campbell et al. | |
| 6,208,974 B1 | 3/2001 | Campbell et al. | |
| 6,347,329 B1 | 2/2002 | Evans | |
| 6,684,188 B1 | 1/2004 | Mitchell et al. | |
| 7,072,840 B1 | 7/2006 | Mayaud | |
| 7,233,938 B2 | 6/2007 | Carus et al. | |
| 7,793,217 B1 | 9/2010 | Kim et al. | |
| 7,916,014 B2 * | 3/2011 | Rapaport | G16H 80/00 340/539.12 |
| 7,983,935 B1 * | 7/2011 | Carricarte | G16H 15/00 705/2 |
| 8,150,711 B2 | 4/2012 | Kelly et al. | |
| 8,311,847 B2 | 11/2012 | Kotula et al. | |
| 2004/0172306 A1 * | 9/2004 | Wohl | G16H 10/60 705/3 |
| 2005/0171817 A1 | 8/2005 | Sachdev et al. | |
| 2005/0273363 A1 | 12/2005 | Lipscher et al. | |
| 2008/0183504 A1 | 7/2008 | Highley | |
| 2012/0035956 A1 | 2/2012 | Cane et al. | |
| 2012/0284603 A1 * | 11/2012 | Saibabu | G16H 10/20 715/224 |
| 2014/0074509 A1 * | 3/2014 | Amarasingham | G16H 50/30 705/3 |
| 2015/0379200 A1 * | 12/2015 | Gifford | G16H 10/60 705/3 |
| 2020/0043579 A1 * | 2/2020 | McEwing | G16H 10/60 |

OTHER PUBLICATIONS http://www.revenuexl.com/dermatology-emr (not admitted to be prior art; last viewed on Aug. 15, 2011).
http://www.allscripts.com/en/company/about-us.html (last viewed on Aug. 15, 2011).
Beittel-Becker Pediatric Associates, LLC, from http://case study.aprima.com/product/casestudies (last viewed on Aug. 15, 2011).
http://www.spectraemr.com/emr-products/emr-and-practice-management-system.php (last viewed on Aug. 10, 2011).
http://edgeehr.com/products/edge_ehr.php (not admitted to be prior art; last viewed on Aug. 15, 2011).
Aprima, "Abandoning Paper To Implement And HER/PM?", Aug. 2009, pp. 1-2.
Australian Patent Application No. 2011286192, Patent Examination Report No. 1, dated Oct. 31, 2013, 3 pages.
Australian Patent Application No. 2011286192, Patent Examination Report No. 2, dated Dec. 9, 2014, 3 pages.
International Search Report for PCT/US2011/045348 filed Jul. 26, 2011; Search completed Dec. 6, 2011; dated Dec. 13, 2011.

* cited by examiner

Progress Note

Chief Complaint: Rash

HPI – This is a 64 year old Female who: comes in for a chief complaint of rash, located on the umbilical skin, right breast, and left cymba. The rash is flaking and burning, and is moderate in severity. The rash has been present for 2 weeks, and is associated with sore throat and fevers. The rash is focal in distribution.

[ Add Addtional HPI Notes ]

Family History of Melanoma: No

Medications:
ZYRTEC
VIAGRA
ALLEGRA

Allergies:
PEANUT (Other:Barf,Fatigue, and Liver toxicity)

ROS:
A full review of systems was performed including Gastrointestinal (G.I.), Psychiatric, Hematologic/Lymphatic, Genitourinary (G.U.), Eyes, Integumentary, Cardiovascular, Respiratory, Constitutional/Symptom, Neurological, Allergic/Immunologic, Musculoskeletal, ENT and Mouth, and Endocrine and was negative except for Changing Mole and Fever or Chills.

Exam:
[ Add Additional Exam Notes]

Impression/Plan:

Fig. 6C

SYSTEM AND METHOD FOR THE RECORDING OF PATIENT NOTES

CROSS-REFERENCE TO RELATED APPLICATIONS

This application is a continuation of U.S. patent application Ser. No. 16/268,929, filed on Feb. 6, 2019, which is a continuation of U.S. patent application Ser. No. 15/235,631, filed on Aug. 12, 2016, which is a continuation of U.S. patent application Ser. No. 13/191,030, filed on Jul. 26, 2011, which claims priority to and the benefit of U.S. Provisional Patent Application No. 61/370,250 filed Aug. 3, 2010, the entire disclosures of each of which are incorporated herein by reference.

FIELD OF THE INVENTION

The invention relates generally to the field of medical records and more specifically to the recordation of patient information.

BACKGROUND OF THE INVENTION

Studies have shown that physicians spend 45% of their time outside of the examination room. A good deal of that time is spent filling out paperwork, such as patient notes and billing documentation. It takes the average physician two minutes to dictate a note. Even computer-literate clinicians take four minutes to record a note using standard electronic medical records software. Therefore, the act of completing a patient record is time consuming.

In addition to the patient health aspects of record keeping, record keeping also has an economic aspect. Payment depends in part on record keeping. For example, the physician must confirm that the correct treatment codes are entered, and that various other required documentation is in place.

Because of these complicated billing requirements, some physicians under-code their billing information. Because these physicians are concerned that mistakes in billing entries might lead to an audit, these physicians will under-code or claim to have done less work than they what was actually performed to avoid missing something in the required documentation.

Conversely, physicians may mistakenly over-code. This occurs when the physician appropriately codes for a certain level visit based on what has occurred during the visit but because he or she has forgotten to enter key components of documentation. The Centers for Medicare and Medicaid Services ("CMS") treats this as an over-code. As far as CMS is concerned, if the documentation is not correct, the examination or procedure did not occur.

The issue then is that note taking and diagnosis session related documentation by a physician is time consuming, fraught with errors and inefficient. To relieve these issues a number of systems exist that provide template patient records into which physicians enter data on the computer. In general, these systems barely reduce the time it takes for a physician to enter a note into the medical record of a patient.

What is needed is an intelligent system that will enter data with minimal physician interaction. The present invention addresses this need.

SUMMARY OF THE INVENTION

In one aspect, the present invention relates generally to a system for recording patient notes by a physician. In one embodiment, the system includes a server comprising: a database; an input module constructed to receive data input from a user, a display module to display notes and note options; and an adaptive notes generation module in communication with the database, the input module and the display module, the adaptive notes generation module receiving input data from the input module and the database and in response to the input data from the input module and the database, automatically generating a plurality of notes and note options. In one embodiment, patient notes can include any diagnosis, insurer, or other patient related data of interest to a physician relative to their practice.

In another embodiment, the notes and note options are medical domain specific. In yet another embodiment, current input from the user modifies subsequent notes and note options automatically generated by the adaptive notes generation module. In still yet another embodiment, clinician preferences learned by the notes generation module modifies the notes and note options automatically generated by the adaptive notes generation module. In another embodiment, the frequency of clinician use determines clinician preferences automatically generated by the system. In yet another embodiment, the system includes one or more of a billing module, a laboratory module and a prescription module.

In one embodiment, the system includes a client computer system in communication with the server input module and the server display module. In another embodiment, the client computer system is keyboardless. In yet another embodiment, the input module and the display module are in communication and permit input from the client using a graphical display. In one embodiment, the system automatically generates a treatment plan in response to input data and database data. In another embodiment, the treatment plan is modifiable by a clinician. In still yet another embodiment, the graphical display produces graphical changes by rollover.

In another aspect, the invention relates to a method of recording patient notes by a clinician. In one embodiment, the method includes the steps of: providing an input screen; inputting data; accessing a database to obtain patient data in response to data input to the input screen; and generating domain specific notes and note options in response to patient data and input to the input screen.

In another embodiment, the method includes the step of modifying the generation of domain specific notes and note options in response to subsequent input. In yet another embodiment, the method includes the step of modifying notes and note options in response to subsequent input further comprises modifying notes and note options in response to clinician preferences. In still yet another embodiment, the method includes modifying the notes and note options in response to clinician preference according to frequency of clinician use. In another embodiment, the method of the system automatically generates a treatment plan in response to the data input and the patient data on the database. In yet another embodiment, the treatment plan is modifiable by a user. In another embodiment, the data input by a user is entered in response a prompt generated in response to metadata associated with an output graphic.

In another aspect, the invention relates to a medium including an executable program, the executable program. In one embodiment, the method includes the steps of providing an input screen on a computer system; inputting data to the computer system; accessing a database on the computer system to obtain patient data in response to data input to the input screen; and generating domain specific notes and note options in response to patient data and input to the input screen.

BRIEF DESCRIPTION OF THE DRAWINGS

The objects and features of the invention can be understood more completely by referring to the drawings described below and the accompanying descriptions.

FIG. 6A is an embodiment of a note history page;

DETAILED DESCRIPTION

The use of headings and sections in the application is not meant to limit the invention; each section can apply to any aspect, embodiment, or feature of the invention.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the invention as if each value were specifically enumerated herein. In addition, smaller ranges between and including the upper and lower limits of a given range are contemplated and encompassed within the invention. The listing of exemplary values or ranges is not a disclaimer of other values or ranges between and including the upper and lower limits of a given range.

Figure 1:
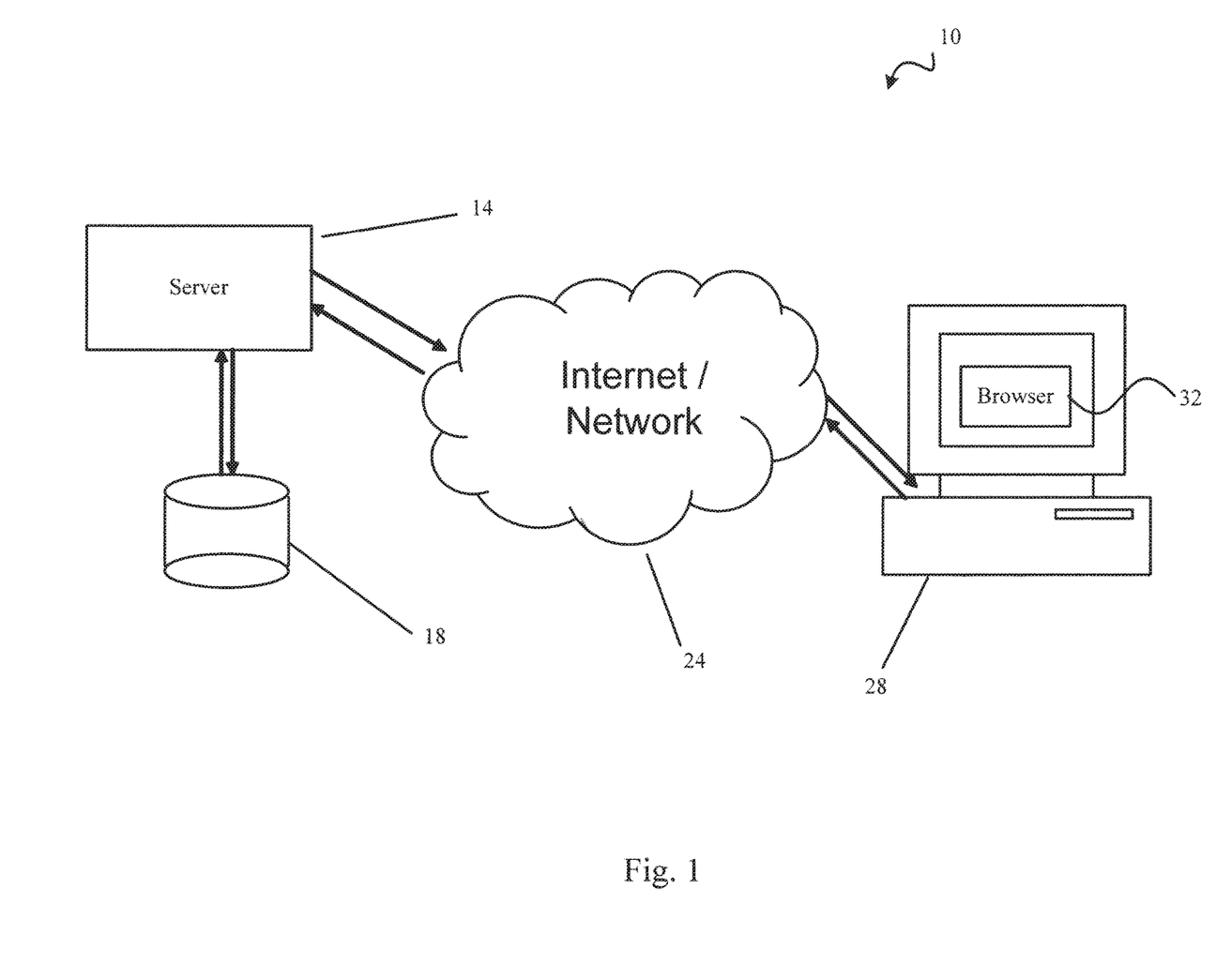
FIG. 1 is a highly generalized schematic diagram of an overview of an embodiment of a system constructed in accordance with the invention.

In brief overview and referring to FIG. 1, a system 10 constructed in accordance with an embodiment of the invention is shown. The system 10 includes a server 14 having a database 18. The server 14 is in communication through a network 24, such as the Internet, with a client 28 having a browser 32. The client can be implemented in software, which is preferred, or hardware. In one embodiment, the browser is the client.

A physician using the system 10 can communicate with the server 14 using any client hardware and software 28 able to support browsing including, without limitation, desktop computers, laptop computers, network computers, tablets, smart phones. In an alternative embodiment, the client is connected directly as a terminal to the server with or without the use of a browser.

Figure 2:
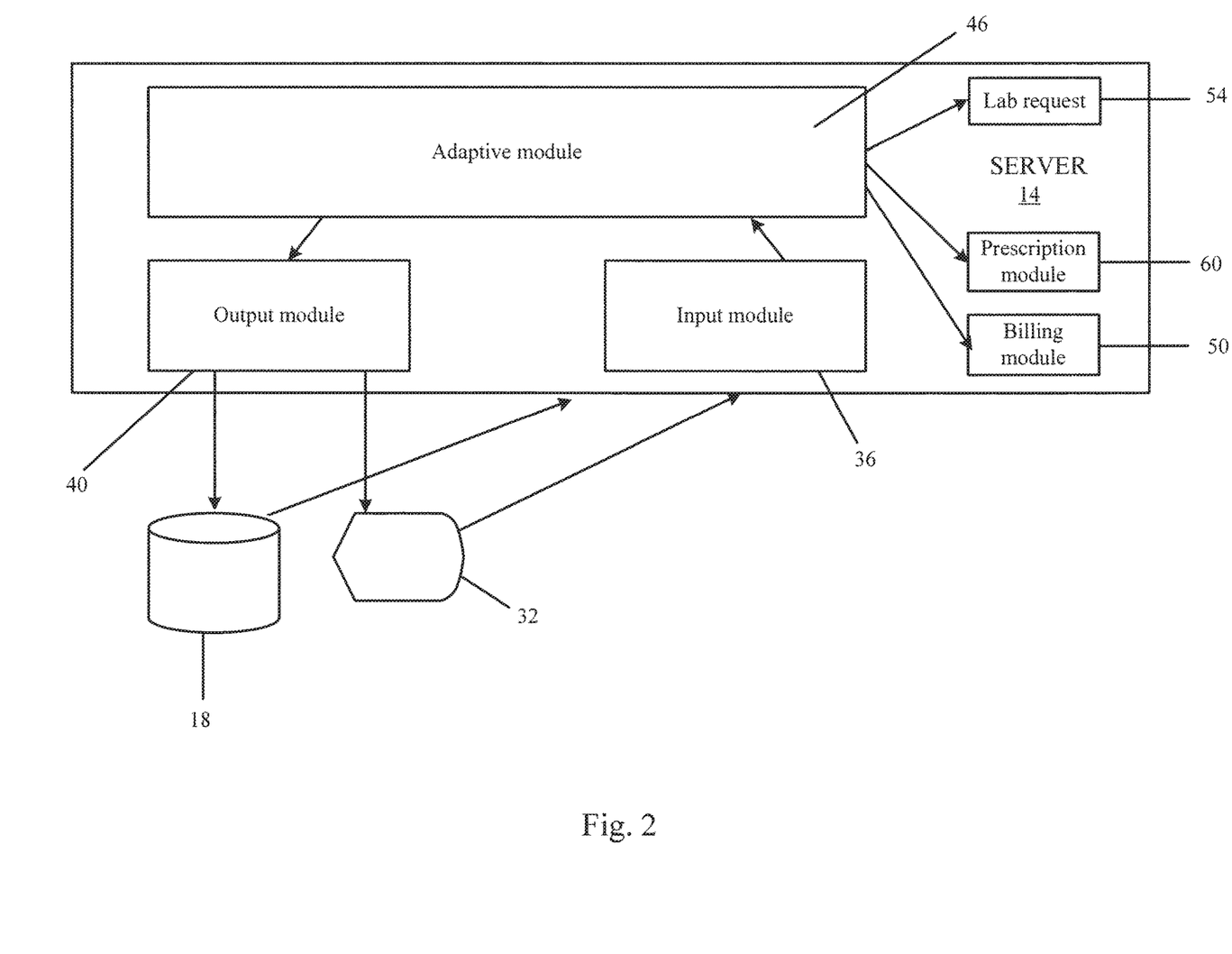
FIG. 2 is a highly generalized schematic block diagram of an embodiment of various software modules constructed in accordance with the invention.

Referring also to FIG. 2, for the purpose of explanation, the server 14 generally includes at least three modules, an input module 36 for obtaining input data from the database 18 and the browser 32; an output module 40 for writing data to the database 18 and the browser 32; and an adaptive notes generation module 46 in communication with the input module 36 and the output module 44. The adaptive notes generation module 46 uses the data input from the browser 32 to obtain additional data from the database 18 not only to construct and populate an output screen for display on the browser 32 but also to create physician notes to be entered as part of the patient record in the database 18.

In addition, the server 14 may include other modules which are in communication with the adaptive note generation module 46 including a billing module 50, a laboratory request module 54, and a prescription module 60. The adaptive note generation module 46 provides the billing codes to the billing module 50 and assures that all the proper documentation is completed. If the adaptive note generation module 46 detects missing information required for payment, the clinician is notified. The adaptive note generation module 46 provides the laboratory request module 54 with requests for laboratory tests and surgical test procedures to be performed on the patient. In turn, the prescription module 58 transmits prescription requests to the pharmacy. Other data collection, processing and transforming modules can also be used in various embodiments.

Figure 3A:
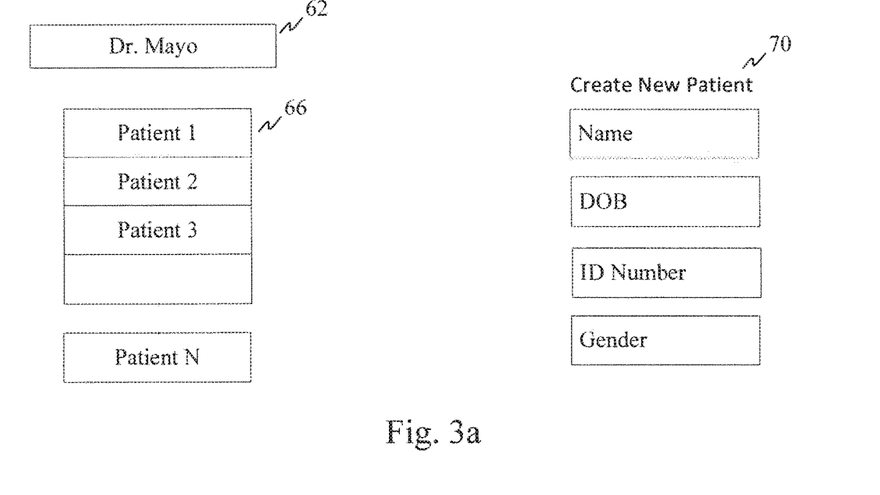
FIGS. 3A and 3B are embodiments of display screens constructed in accordance with the invention.
Figure 6B:
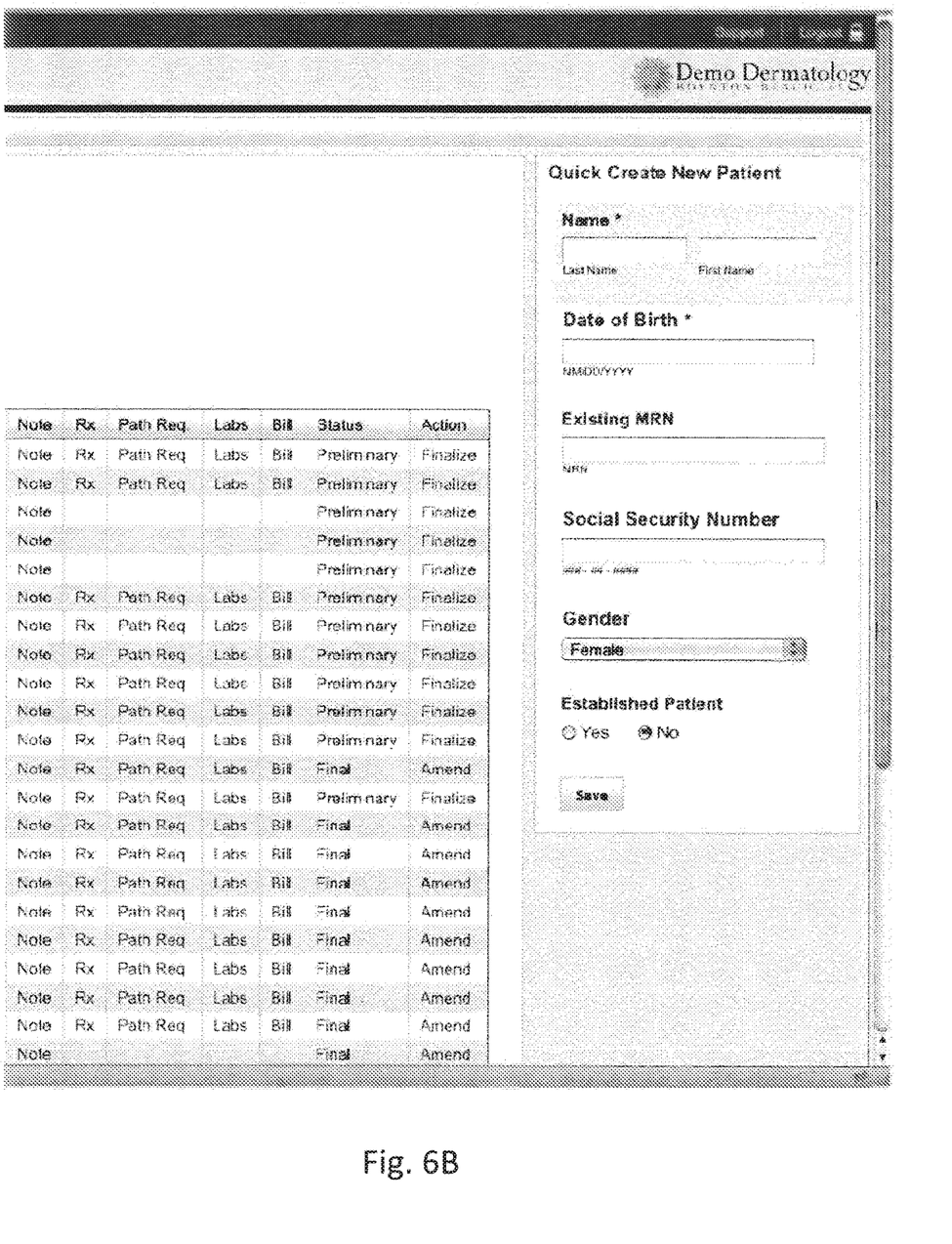
FIG. 6B is an embodiment of a new-patient creation interface.

To better understand the operation of the system 10, it is useful to consider how a clinician would use the system. Referring to FIG. 3A, upon accessing the system with the browser the clinician can obtain from the database a list of all the patients for which the system has knowledge using a mouse click. The clinician begins by logging in by selecting his or her name from a list of clinicians 62. By placing the cursor over a patient name in a list of patients 66 and entering the virtual exam function of the system, the system populates the output screen with data from the patient's electronic record containing prior examination notes. An example of such data is shown in FIG. 6A. Alternatively the physician can enter new patient data in the create-new-patient area 70 (FIG. 6B).

Figure 3B:
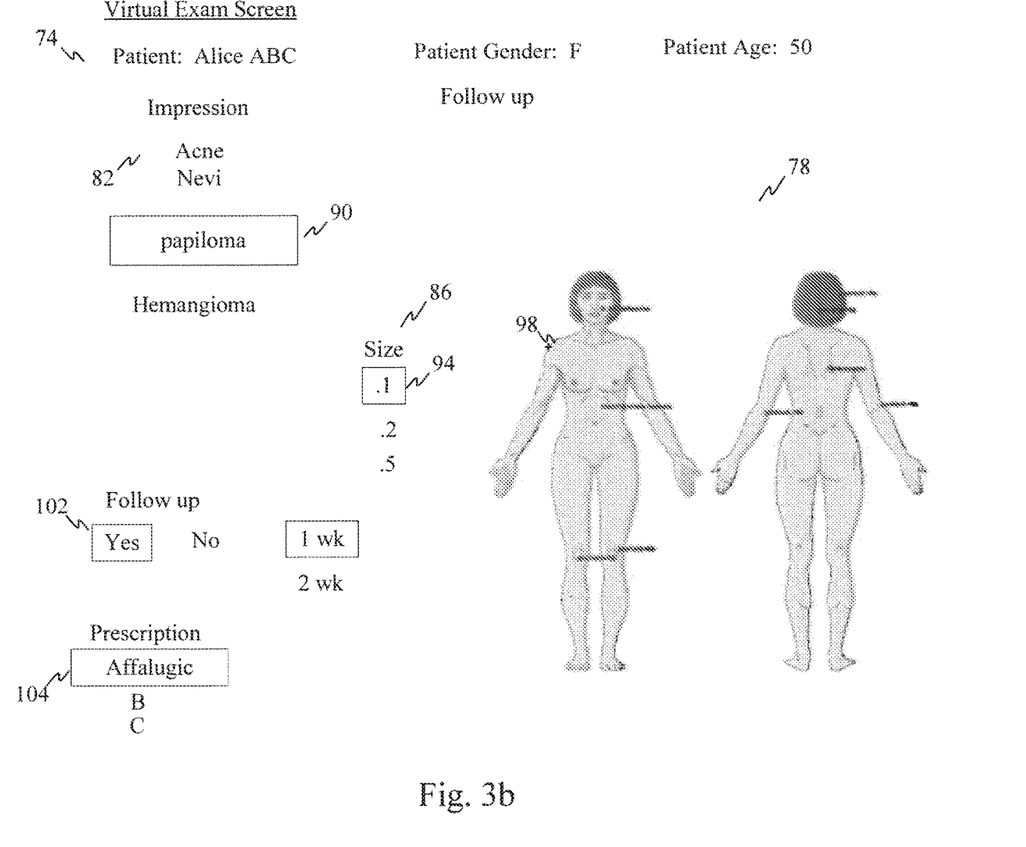

The clinician then enters the virtual exam screen (FIG. 3B). In addition to pre-populating the patient data on the screen 74, the system selects the correct graphic interface 78 for the patient, in this case female, because the patient is female; the correct domain diagnostic information 82, in this case dermatology, because the clinician is a dermatologist; and the correct pop-up windows 86 with note options for the diagnosis.

The clinician using the mouse, or his finger for a touch screen system, can then click on (or touch) the diagnosis or impression list to select the appropriate entries, for example papiloma 90, pop-up window with additional data consistent with the diagnosis, such as the correct size of the lesion, (for example 0.1 mm diameter) 94 and the location on the graphic locating the lesion, for example left shoulder 98. By clicking or touching the location of the problem on the female graphic, the system knows the location of the medical problem. The clinician may also move the cursor over an area (rollover) of the graphic to obtain higher resolution or to obtain another view of the area. On these selections are made, in one embodiment a detailed report and insurer information codes are generated using historic data regarding the general preferred report format of the clinician.

The clinician can then schedule follow-up 102 visit including selecting the follow-up period; request other lab work and procedures and write prescriptions 104. The system keeps track of the physician's preferences automatically and will propose those preferences first to the clinician in the parameter windows. For example, if the clinician most frequently prescribes the drug Adoxa® for the treatment of acne, the system will place Adoxa® at the top of the prescription list in the prescription window. Similarly, if the clinician typically requests a biopsy when a papiloma is diagnosed, then biopsy is placed at the top of the procedures list. Further, another window is the opened so that the type of biopsy can be specified. The specific details (metadata) of the biopsy performed are collected with the information or choices provided defaulting to the clinician's anticipated selections. Various artificial intelligence, genetic or other learning algorithms can be used to accomplish this process. The accuracy of the anticipated selections rapidly increases as the clinician uses the system.

Once completed and saved, the system completes the notes in the results window using standard medical terminology. So in this example the system would generate the following notes: "The patient a 50 year old female presented with a 0.1 mm diameter papiloma on the left scapular region. A biopsy of the papiloma was ordered and the patient was scheduled for a follow-up visit in one week." Thus, by using a few mouse clicks (or in touches or gestures in the case of a touch screen interface) a thirty-seven word note was generated in a matter of seconds. In addition, the system generates the biopsy request, schedules the request for follow-up, and provides the billing information required.

Figure 4A:
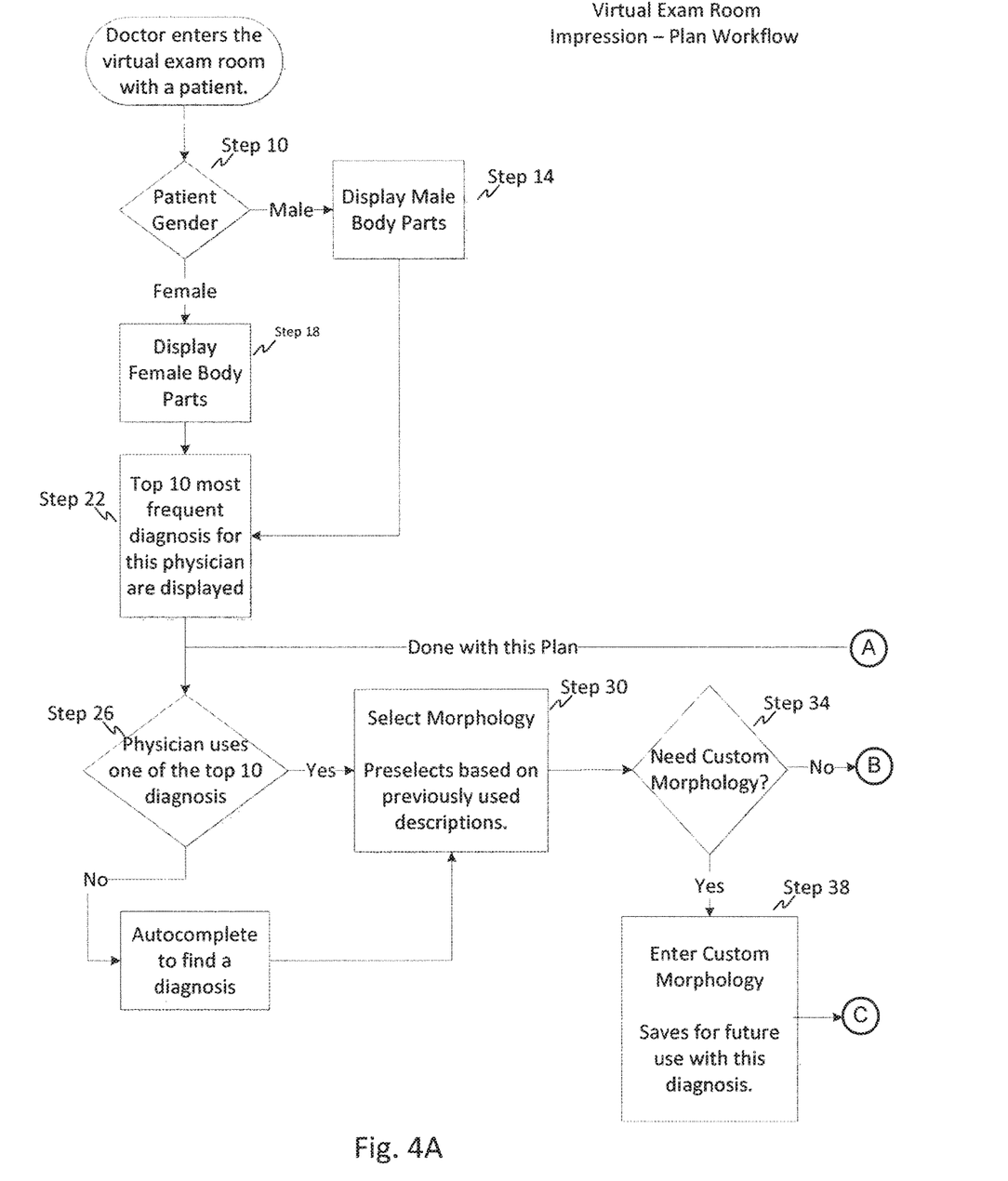
FIGS. 4A and B is a flow diagram of an embodiment of workflow for a virtual examination.
Figure 4B:
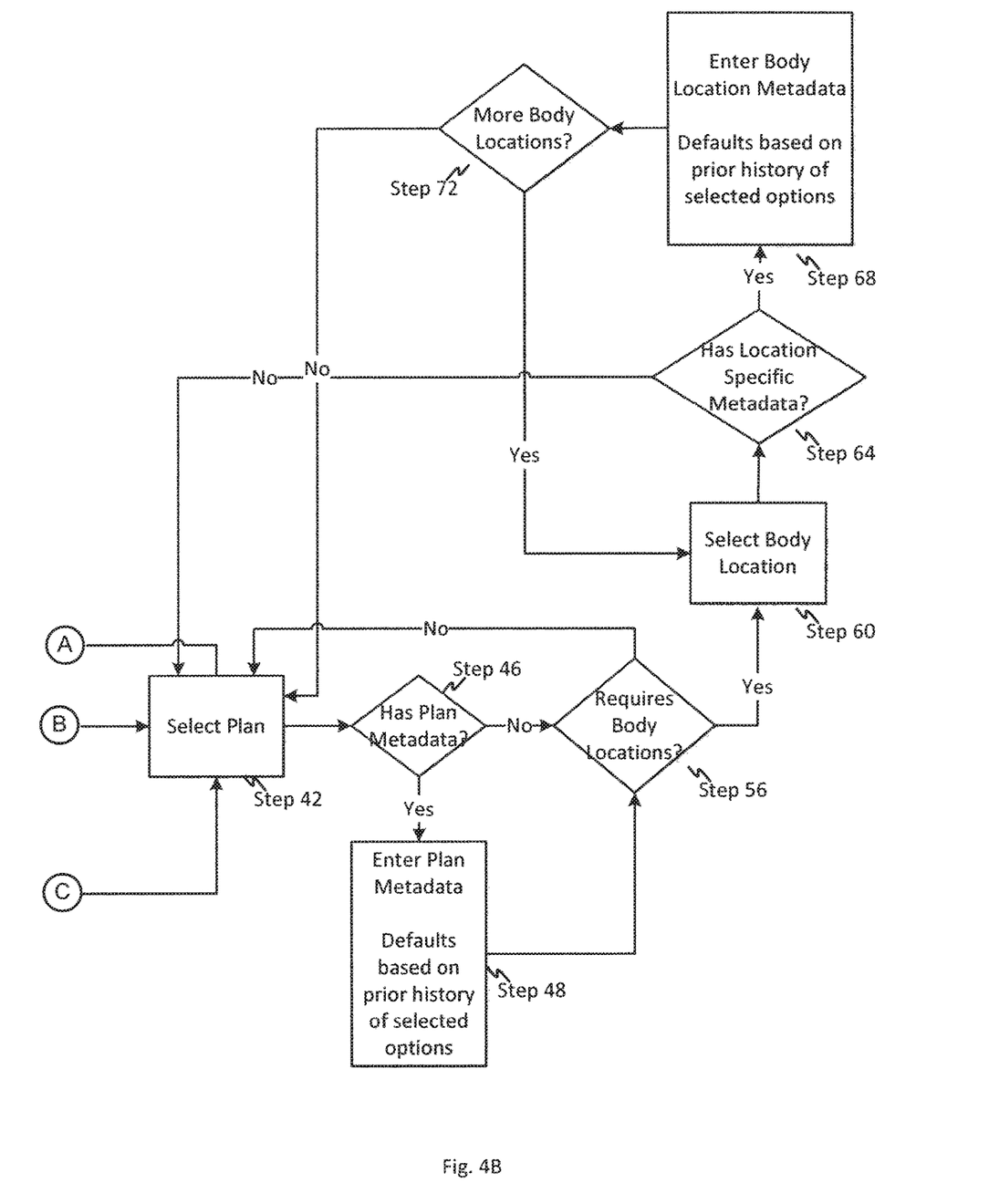

To understand more completely how the system functions, and considering FIGS. 4A and B, the workflow for the virtual exam is shown. The system determines the patient's gender from the information associated with the patient in the database (Step 10). If the patient is male, the male graphics are rendered (Step 14); while if female, the female graphics are rendered (Step 18).

Based on who the clinician is, the system lists the ten most frequent diagnoses by this clinician (Step 22) in the diagnostic window. The system determines this by keeping statistics about the clinician's practice. When the clinician selects a diagnosis (Step 26), the clinician is then presented with a list of morphologies, (Step 30), again based on the clinician's previously used descriptions from the database. If no morphology meets the requirements a custom morphology (Step 34) is selected and entered into the database for future use (Step 38).

If a custom morphology is not required then a plan is selected (Step 42). The listing of possible plans is dependent on the selected diagnosis and can be ordered based on anticipated use. Thus, the number of possible choices is limited based on domain knowledge.

Once a plan has been selected, if the plan requires additional information to be collected (metadata) the clinician is prompted to further describe the plan. The plan's metadata is set to a default option based on the clinician's anticipated selections (Step 48). An example of a plan which prompts for metadata is using Glycolic Acid to treat Acne. The clinician would be prompted to enter a dilution percent and duration. While the possible dilution percents could be 35%, 50%, and 70%, the system will default the selection based on the clinician's anticipated defaults. Duration in this example could be anywhere from 1 to 60 minutes, again defaulting to the clinician's anticipated selection.

If the plan requires the notation of a body location (Step 56) the system inputs the location data from the graphic (Step 60) and acquires the location metadata (Step 68) if required by the plan (Step 64). An example of location-specific procedure metadata is performing a punch biopsy on a selected body location. The clinician would be prompted to enter information specific to this biopsy site which would include, but not be limited to, punch size, biopsy type, anesthesia type, anesthesia volume, suture type, would care instructions, and suture removal duration. The body location specific metadata is defaulted based on the clinician's anticipated selections which could take into account the clinician's anticipated preferences, the selected procedure, the location on the body, and other factors. The clinician then determines if more locations are needed (Step 72), and if not goes to select a new plan (Step 42).

Figure 5A:
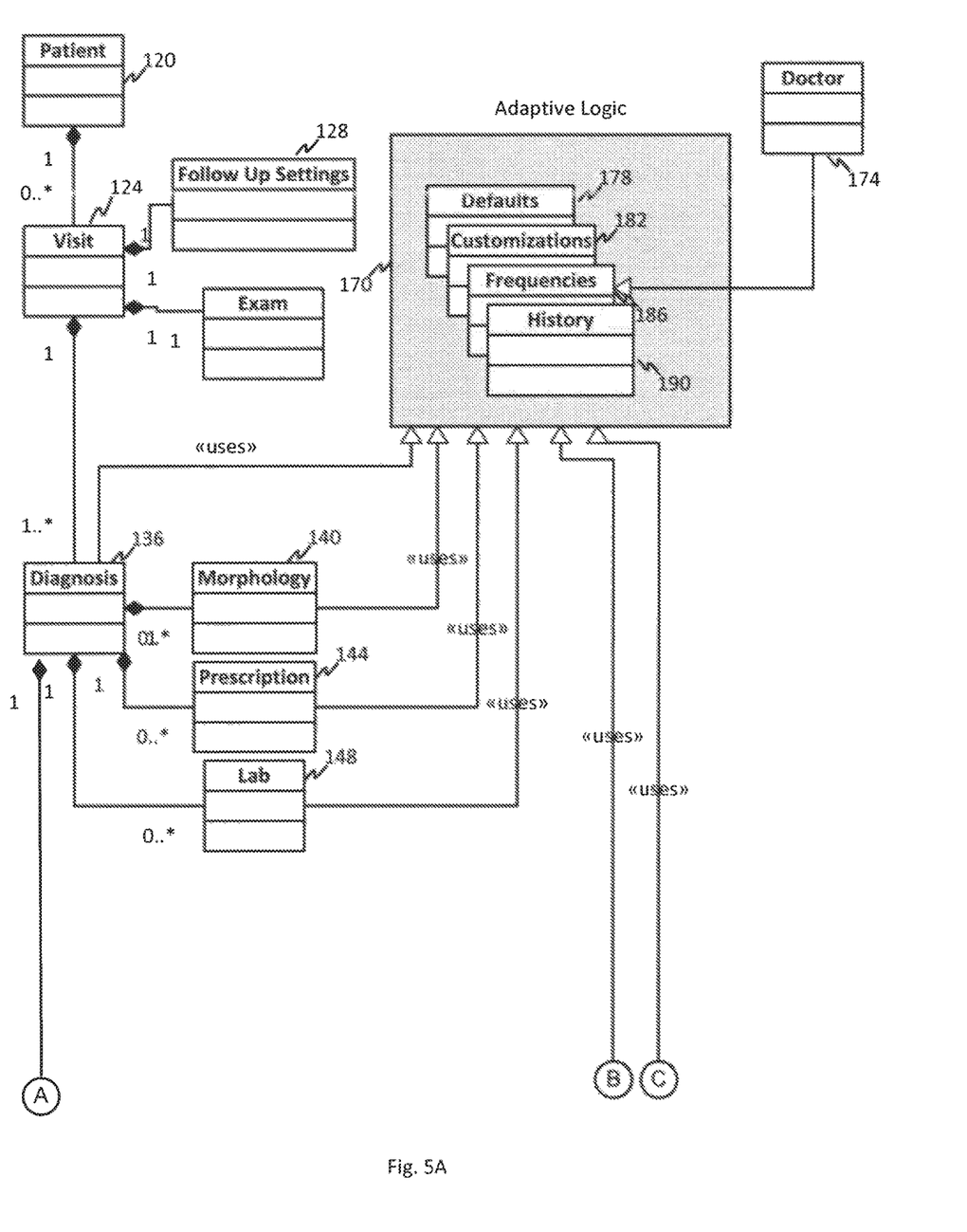
FIGS. 5A and B is an embodiment of a data schema constructed in accordance with the invention.
Figure 5B:
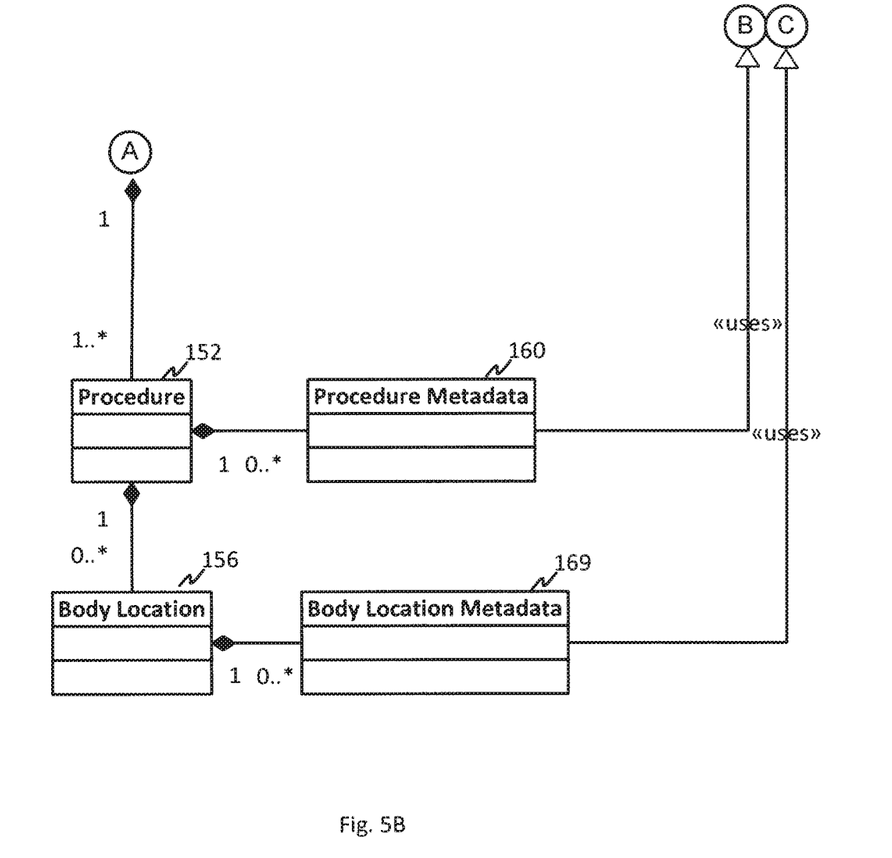

Referring to FIGS. 5A and B, the adaptive note generating module of the system is capable of performing these functions in part because of the data schema that is used in organizing the patient information and requesting information during the examination. The patient table 120 is linked to visit information such as date and time 124. A follow-up visit duration and purpose can be linked to this visit 128.

The diagnosis table 136 is linked to the visit data so that changes over time can be tracked. Several other data types are linked to the type of diagnosis 136. For example, the diagnosis may contain morphologies 140 (for example to describe the size and color of a lesion), a prescriptions 144 for treatment of the lesion, lab tests 148 to further confirm the diagnosis, and procedures 152, such as a biopsy, to confirm a diagnosis.

If a procedure 152 is required, it may contain one or more locations of the procedure (that is, the lesion location) 156. The procedure 152 could have metadata 160 associated with it, such as the dilution percentage of glycolic acid. For each selected location, metadata 169 might be collected. For example, the specifics for a punch biopsy may be included.

Figure 6C:
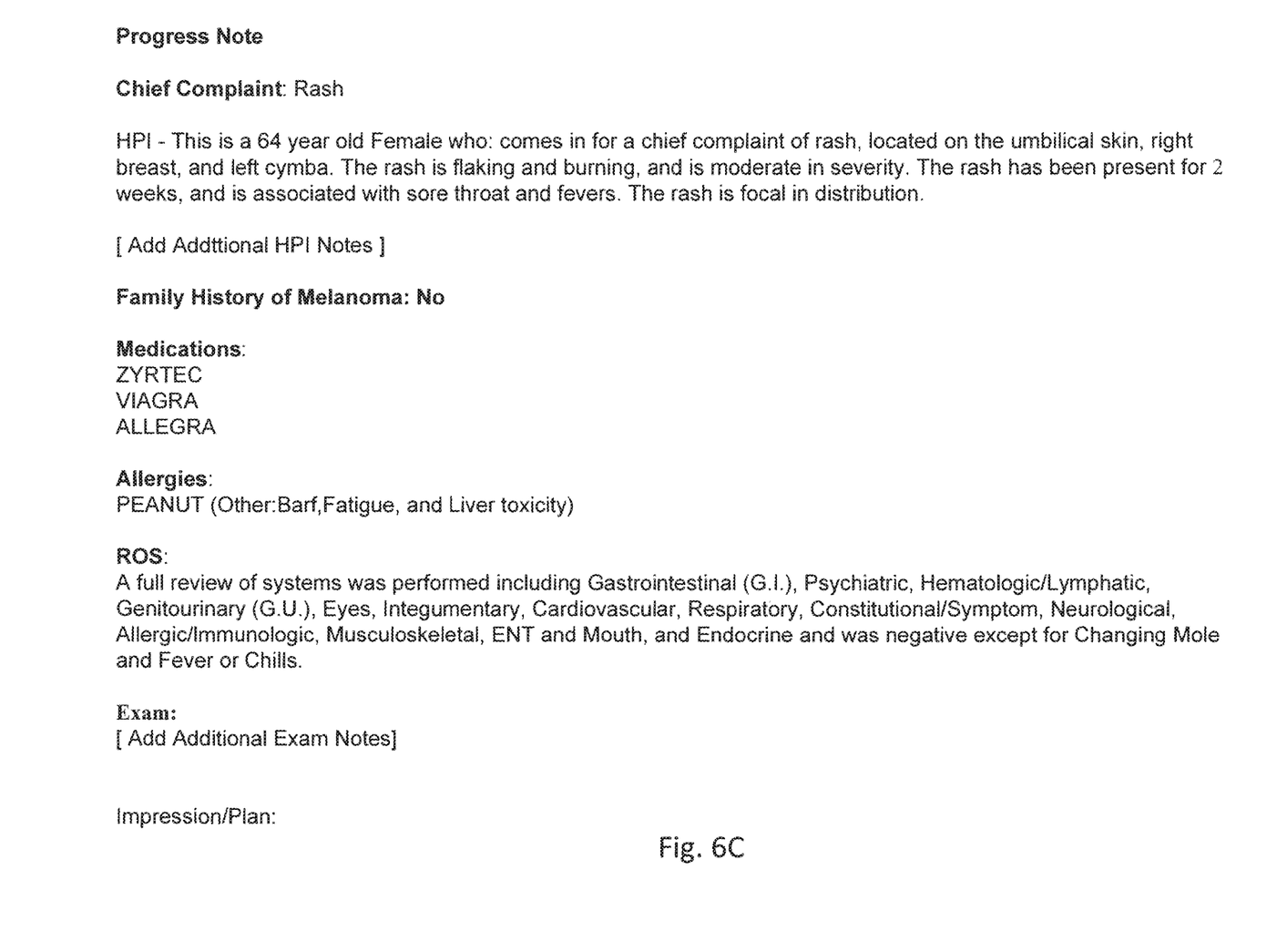
FIG. 6C is an embodiment of a progress note page generated in response to a small number of clinician inputs relative to the data displayed in the progress note.

The morphologies 140, prescriptions 144, labs 148, procedure metadata 160, and location metadata 169 all obtain information from the adaptive logic module 170. The data for the adaptive logic module 170 is determined in part by the identity of the clinician 174. The adaptive logic module 170 maintains information on default parameters 178 (the values used by the system until enough history about the physician has been acquired), any customizations required by the clinician 182, such as specific morphology descriptions entered by the clinician, the frequencies of parameters selected by the physicians 186 (for example the drugs used by the physician to treat various diseases, and the history 190. In one embodiment, history is the last previously set value(s). This is the case because sometimes the most frequently used value is not correct, such as when a new standard of care is introduced. Under those circumstances, a clinician wants the most recent settings used, not the most frequently used. This selection between most recent settings and historic settings can be handled using the software embodiments described herein. This schema permits the notes to be tailored to the physician thereby increasing the efficiency of input by reducing the number of mouse clicks, gestures or screen touches to generate a note (FIG. 6C).

As an example, when a patient arrives the patient's history is taken on an iPad® while the previous patient is being seen. Assume for this example the patient is a 35 year old woman with a history of limited plaque psoriasis who presents with a non-healing lesion on her left nasal ala.

In the examination room the visit is documented in real time. For example, the entry might be: "On examination there is a waxy telangetatic papule on the left nasal ala and psoriasiform plaques with micaceous scale." In addition, a diagnostic and therapeutic procedure is performed. The system provides a template to enter both the result of the examination and the request for medical tests.

No single template is appropriate for each clinician. In one embodiment of the system, over 500 dermatologic diagnoses are programmed into EMA Because a dermatologist in Alaska may see more chilblains while a dermatologist in Florida may see more sunburns, EMA learns how the physician practices and shows the physician the most frequent histories and diagnoses by quickly adapting to each physician's style. For example EMA can remember laser settings, units of Botox® used for a given area of the face, and even the clinician's choices of anesthesia and suture for biopsies. Anything input once is remembered by EMA. Like a medical assistant, EMA anticipates what the clinician needs without the clinician asking for it.

The present invention may be embodied in may different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other PLD), discrete components, integrated circuitry (e.g., an Application Specific Integrated Circuit (ASIC)), or any other means including any combination thereof. In a typical embodiment of the present invention, predominantly all of the communication between users and the server or software as a service provider is implemented as a set of computer program instructions that is converted into a computer executable form, stored as such in a computer readable medium, and executed by a microprocessor under the control of an operating system.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as JAVA, Javascript, DHTML, AJAX, CSS, XML, SQL, HTML, Fortran, C, or C++) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth®), networking technologies, and internetworking technologies. The computer program may be distributed in any form as a removable storage medium with accompanying printed or electronic documentation (e.g., shrink wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL). The embodiments described herein may use any suitable input device or user interface whether touch screen based or based upon mouse clicks or other recognizable user inputs. For example, in one embodiment, a laptop, a mobile device, a table computer, an iPad®, an iPhone®, or other suitable devices can be used as appropriate to facilitate a clinician's data collection and processing efforts.

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth®), networking technologies, and internetworking technologies. The programmable logic may be distributed as a removable storage medium with accompanying printed or electronic documentation (e.g., shrink wrapped software), preloaded with a computer system (e.g., on system ROM or fixed disk), or distributed from a server or electronic bulletin board over the communication system (e.g., the Internet or World Wide Web). In one preferred embodiment, a software as a service implementation with remote data storage and encryption is used.

The examples presented herein are intended to illustrate potential and specific implementations of the invention. It can be appreciated that the examples are intended primarily for purposes of illustration of the invention for those skilled in the art. There may be variations to these diagrams or the operations described herein without departing from the spirit of the invention. For instance, in certain cases, method steps or operations may be performed or executed in differing order, or operations may be added, deleted or modified.

Variations, modification, and other implementations of what is described herein will occur to those of ordinary skill in the art without departing from the spirit and scope of the invention as claimed. Accordingly, the invention is to be defined not by the preceding illustrative description, but instead by the spirit and scope of the following claims.

What is claimed is:

1. A system for recording patient information by a user and automatically generating patient notes for a clinician, the system comprising:
    a server comprising:
        one or more processors;
        a database, executing on the one or more processors, comprising clinician preference data, patient data, and metadata;
        an input module, executing on the one or more processors, constructed to receive data input from the user and store it as patient data in the database;
        a display module, executing on the one or more processors, to display notes, note options and reports; and
        an adaptive notes generation module, executing on the one or more processors, in communication with the database, the input module and the display module, the adaptive notes generation module receiving input data from the user through the input module and provider preference data, patient data, and metadata from the database and in response to the input data from the input module and the clinician preference data, patient data, and metadata from the database, automatically generating a plurality of notes, note options, and reports using adaptive learning in response to clinician preference data, patient data, and metadata,
        wherein data is input and stored as objects that are interpretable by the adaptive notes generation module to generate a natural language structured display of the clinician's preferences in response to the metadata of each datum.

2. The system of claim 1 wherein the notes and note options are medical domain specific.

3. The system of claim 1 wherein current input from a user modifies subsequent notes and note options automatically generated by the adaptive notes generation module.

4. The system of claim 3 wherein past clinician preferences learned by the adaptive notes generation module modifies the notes and note options automatically generated by the adaptive notes generation module.

5. The system of claim 4 wherein the frequency of clinician use of a past clinical preference determines the clinician preferences automatically generated by the system.

6. The system of claim 1 further comprising at least one of a billing module, a prescription module, and a lab module.

7. The system of claim 1 further comprising a client computer system in communication with the server input module and the server display module.

8. The system of claim 7 wherein the client computer system is keyboardless.

9. The system of claim 8 wherein the input module and the display module are in communication and permit input from the client computer system using a graphical display.

10. The system of claim 9 wherein the graphical display produces graphical changes by rollover.

11. The system of claim 1 wherein the system automatically generates a treatment plan in response to input data and database clinician preference data, patient data, and metadata.

12. The system of claim 11 wherein the treatment plan is modifiable by a clinician.

13. A method of recording patient information by a user and generating patient notes by an automated system for a clinician, the method comprising:
    displaying an input screen on a computer system;
    inputting, using the automated system, clinician preference data, patient data, and metadata to the computer system, wherein clinician preference data, patient data, and metadata is input and stored as objects that are interpretable by an adaptive notes generation module to enable a structured display of the clinician's preferences;
    accessing a database on the computer system to obtain patient data in response to data input to the input screen; and
    generating domain specific structured natural language notes, note options and reports, using the automated system, in response to patient data, and past clinician preferences and metadata for each datum; and
    displaying one or more of the domain specific structured natural language notes, note options and reports using one or more user interface screens.

14. The method of claim 13 further comprising modifying the generation of domain specific notes and note options in response to subsequent input.

15. The method of claim 14 wherein the step of modifying notes and note options in response to subsequent input further comprises modifying notes and note options in response to past clinician preferences.

16. The method of claim 15 wherein the notes and note options are modified in response to a clinician preference according to frequency of clinician use.

17. The method of claim 1 further comprising automatically generating a treatment plan in response to the data input and the patient data on the database.

18. The method of claim 17 wherein the treatment plan is modifiable by a user.

19. The method of claim 1 wherein the data input by a user is entered in response a prompt generated in response to metadata associated with an output graphic.

20. The system of claim 1 wherein the adaptive notes generation module determines what metadata is necessary for the adaptive notes generation module to perform its function and if that metadata is missing, notifies the clinician as to the problem.

21. The system of claim 1 wherein the adaptive notes generation module determines what graphical user interface to use in response to patient data.

22. The system of claim 1 wherein the adaptive notes generation module determines what drug to prescribe in response to patient data.

23. The system of claim 1 wherein the adaptive notes generation module generates a plurality of entry options as a hierarchy of clinician preferences and determines a hierarchy by a response to a previous entry in the hierarchy.

* * * * *